(12) United States Patent
Schoepp et al.

(10) Patent No.: US 12,349,981 B2
(45) Date of Patent: Jul. 8, 2025

(54) FIELD GENERATOR ASSEMBLY AND METHOD FOR SURGICAL NAVIGATION

(71) Applicant: Stryker European Operations Limited, Carrigtwohill (IE)

(72) Inventors: Hans Schoepp, Freiburg (DE); Florian Herrmann, Schwanau (DE)

(73) Assignee: Stryker European Operations Limited, Carrigtwohill (IE)

( * ) Notice: Subject to any disclaimer, the term of this patent is extended or adjusted under 35 U.S.C. 154(b) by 507 days.

(21) Appl. No.: 17/223,707

(22) Filed: Apr. 6, 2021

(65) Prior Publication Data
US 2021/0338338 A1 Nov. 4, 2021

(30) Foreign Application Priority Data

Apr. 29, 2020 (EP) .................................... 20172144

(51) Int. Cl.
*A61B 34/20* (2016.01)
*G01D 5/14* (2006.01)
*A61B 90/50* (2016.01)

(52) U.S. Cl.
CPC .............. *A61B 34/20* (2016.02); *G01D 5/14* (2013.01); *A61B 2034/2051* (2016.02); *A61B 2090/502* (2016.02)

(58) Field of Classification Search
CPC .............. G01D 5/14; A61B 2034/2051; A61B 2090/502
See application file for complete search history.

(56) References Cited

U.S. PATENT DOCUMENTS

| | | | |
|---|---|---|---|
| 5,829,444 A | 11/1998 | Ferre et al. | |
| 8,150,497 B2* | 4/2012 | Gielen | A61B 34/20 600/407 |
| 8,473,026 B2 | 6/2013 | Ferre et al. | |
| 2014/0135746 A1 | 5/2014 | Schoepp | |
| 2014/0194734 A1 | 7/2014 | Birkenbach et al. | |
| 2014/0275987 A1 | 9/2014 | Bzostek et al. | |
| 2016/0331269 A1 | 11/2016 | Kruger et al. | |
| 2019/0282305 A1 | 9/2019 | Shameli et al. | |

FOREIGN PATENT DOCUMENTS

EP 3120799 A1 1/2017

* cited by examiner

*Primary Examiner* — Walter L Lindsay, Jr.
*Assistant Examiner* — Milton Gonzalez
(74) *Attorney, Agent, or Firm* — Howard & Howard Attorneys PLLC (57) ABSTRACT

A field generator assembly for surgical navigation is provided. The field generator assembly comprises a field generator configured to generate an electromagnetic field, an attachment member configured to attach the field generator to a body of a patient, at least one first arm comprising a first portion configured to be in contact with a surface of the body of the patient when the field generator is attached to the body, and a second portion movably attached relative to the field generator, and at least one sensor configured to measure a spatial relationship between the at least one arm and the field generator. Also provided is a method of obtaining a relative pose between a surface of the body and a field generator.

13 Claims, 5 Drawing Sheets

FIELD GENERATOR ASSEMBLY AND METHOD FOR SURGICAL NAVIGATION

PRIORITY CLAIM

This application claims priority under 35 U.S.C. § 119 to European Patent Application No. 20172114.6-1122, filed Apr. 29, 2020, the entire contents of which are hereby incorporated by reference.

TECHNICAL FIELD

The present disclosure generally relates to surgical navigation. A field generator assembly for surgical navigation is provided. Further provided is a method of obtaining a relative pose between a surface of a body of a patient and a field generator of the field generator assembly. Also provided are a computer program and a carrier containing the computer program.

BACKGROUND

In surgical navigation, a pose (i.e., at least one of a position and an orientation) of a surgical instrument or other medical component (e.g., a bone plate of implant) often needs to be displayed relative to patient image data. The patient image data may be computed tomography (CT) image data, magnetic resonance (MR) image data or the like.

Surgical navigation relies on tracking systems which comprise a tracking unit to localize mobile trackers relative to the tracking unit. The trackers may be attached to different components that are to be tracked by the tracking unit in an operating room. Different types of trackers are known in the art, such as active or passive optical markers or electromagnetic sensors. In the case of optical markers, the tracking unit is a (e.g., stereoscopic) camera of an optical tracking system. In the case of electromagnetic sensors, the tracking unit may be a localizer of an electromagnetic tracking system, the localizer being communicatively coupled to the electromagnetic sensors.

One or more trackers may, for example, be attached to a surgical instrument, and the tracking system may provide a pose of the attached electromagnetic sensors relative to the camera, or, in case of the electromagnetic tracking system, relative to an electromagnetic field generator. Based on the pose provided by the tracking system, a pose of the surgical instrument relative to the camera or relative to the field generator may be determined. In order to obtain the pose of the surgical instrument relative to the patient image data, a registration between the camera or the field generator and the patient image data needs to be known or determined. In particular, this registration may be used to translate the pose of the surgical instrument relative to the camera or the field generator into a pose of the surgical instrument relative to the patient image data.

To obtain the registration between the field generator and the patient image data, a pose of the body of the patient relative to the field generator may be determined. Subsequently, the determined pose of the body may be matched with the patient image data to obtain the registration.

There are several possibilities of how to determine the pose of the body of the patient relative to the field generator. Some approaches rely on manually defining different registration points on a surface of the patient's body with a pointer tracked by the (e.g., electromagnetic) tracking system. Other approaches rely on manually attaching trackers onto different registration points on the surface of the patient's body. Tracked positions of the registration points relative to the field generator may then be matched with a model surface of the patient's body defined by the patient image data to obtain the registration.

These and other approaches may lead to registrations with different accuracies depending on the number and placement of the registration points. For example, the registration points may lie on different parts of the body depending on the surgeon's preference and patience, yielding registrations with varying and often low accuracies. Also, it may not be possible to track registration points on parts of the body which lie outside an electromagnetic field detection range of the electromagnetic sensors, thereby decreasing flexibility in registration point placement and accuracy of obtained registrations.

Corresponding prior art is known from U.S. Pat. No. 5,829,444 A1 and U.S. Pat. No. 8,473,026 B2 as well as US 2014/0135746 A1.

SUMMARY

There is a need for a technique that solves one or more of the aforementioned or other problems in the context of electromagnetic surgical navigation that relies on a field generator configured to generate an electromagnetic field.

According to a first aspect, a field generator assembly for surgical navigation is provided. The field generator assembly comprises a field generator configured to generate an electromagnetic field and an attachment member configured to attach the field generator to a body of a patient. The field generator assembly further comprises at least one first arm. The at least one first arm comprises a first portion configured to be in contact with a surface of the body of the patient when the field generator is attached to the body, and a second portion movably attached relative to the field generator. The field generator assembly further comprises at least one sensor configured to measure a spatial relationship between the at least one arm and the field generator.

The spatial relationship between the at least one arm and the field generator may comprise or consist of a pose (i.e., at least one of a position and an orientation) of (e.g., a portion or part of) the at least one arm relative to the field generator. The measurement of the at least one sensor may represent or be used to determine a pose of the first portion relative to the field generator. The first portion in contact with the surface of the body may be used as a registration point or area for matching a pose of a surface of the patient's body to patient image data. The pose of the first portion relative to the field generator may be defined by physical properties (e.g., dimensions, material and the like) of the at least one arm. Alternatively or additionally, the pose of the first portion relative to the field generator may be defined by at least one of a shape and pose of the surface of the patient's body.

The at least one arm may be formed as an elongate member. The first portion may be a first end portion of the at least one first arm. The first end portion may be formed as a tip of the at least one first arm. The at least one arm or the first portion may be arranged on a first side of the body when the field generator is attached to the body. The field generator may be arranged on a second side of the body when the field generator is attached to the body. The first side may be opposite to the second side.

The first side may be an anterior side. The second side may be a posterior side. The field generator assembly may be configured such that the body of the patient lies at least partially between the field generator and the at least one arm or at least partially between the field generator and the first portion, when the field generator is attached to the body.

The second portion may be a second end portion of the at least one first arm. The second portion may be formed as a connection element of the at least one first arm. This may enable a large distance of, e.g., more than 5 cm or more than 10 cm between the first portion and the second portion, thereby ensuring a large distance of, e.g., more than 10 cm or more than 15 cm between the first end portion and the field generator.

The attachment member may comprise or consist of an adjustable band such as a headband (also referred to as head strap) or a breast strap. The attachment member may comprise or consist of the at least one first arm (e.g., of two or more arms).

The first portion may be configured to be tensioned (e.g., spring-biased) against the surface of the body of the patient when the field generator is attached to the body. The first portion may be configured to urge (e.g., press or push) in direction of the field generator, at least when the field generator is attached to the body. The first portion may be configured to be tensioned against the surface of the body on the first side of the body, for example the anterior surface, when the field generator is attached to the body, for example on the second side of the body. The field generator assembly, for example the first arm, may comprise one or more elastic members tensioning the first portion against the surface of the body. The first arm may be made of an elastic material and configured to tension the first portion against the surface of the body. The contact force between the first portion and the surface of the body may be equal to or lower than a first predetermined force, wherein the first predetermined force may be chosen to avoid an injury of the patient. The contact force between the first portion and the surface of the body may be equal to or higher than a second predetermined force, wherein the second predetermined force may be chosen to ensure a stable (e.g., stationary over a certain time) contact of the first portion and the surface of the body.

The first portion may be configured to be in contact with a surface of a predetermined landmark of the surface of the body of the patient when the field generator is attached to the body. The predetermined landmark may be a point, an area or a shape of a part of the body that is capable of being, e.g., automatically, extracted or identified in the patient image data. The surface of the predetermined landmark may be a point or an area of the surface of the body that is determined to be advantageous or optimal for matching the pose of the patient's body to the patient image data. The predetermined landmark may be an anatomical body part or organ such as a nose, an ear, an eye or the like.

The at least one first arm may comprise the first portion multiple times, for example twice or three times. In other words, the at least one first arm may comprise a plurality of first portions. Each of the plurality of first portions is configured to be in contact with the surface of the body of the patient when the field generator is attached to the body. For example, the at least one first arm comprises a hand having three fingers, each finger comprising one of three first portions comprised in the at least one arm. The at least one first arm may in addition or alternatively to the hand comprise a plurality of protrusions, each protrusion comprising one of the plurality of first portions. In the following, in case it is referred to the "first portion", this shall comprise the meaning "each, all or at least one of the plurality of first portions".

The field generator assembly may further comprise a second arm connected to the first arm to be movable together with the first arm. The two arms together with the field generator may thus form a kind of loop.

The field generator assembly may further comprise a third arm, wherein the at least one first arm and the third arm are located on opposite sides relative to the field generator. The field generator assembly may comprise a number of third arms corresponding to a number of first arms. The third arm may be connected to the first arm to be movable together with the first arm. The field generator assembly may comprise at least one sensor configured to measure a pose of the third arm relative to at least one of the at least one arm and the field generator. The third arm may comprise a first portion configured to be in contact with a surface of the body of the patient when the field generator is attached to the body, and a second portion movably attached relative to the field generator. The third arm may comprise the first portion multiple times, as described above with respect to the first arm.

The attachment member may be configured to attach the field generator to a posterior side of a head of the patient. The field generator may be configured to generate an electromagnetic field enclosing at least the sensor(s) of the field generator assembly when the field generator is attached to the body of the patient. The electromagnetic field may further enclose at least the head of the patient.

At least one of the at least one first arm, the second arm and the third arm may be attached to the field generator or a casing (i.e., receptacle) thereof via a joint so as to be movable relative to the filed generator. At least one of the at least one first arm, the second arm and the third arm may be configured to be (e.g., only) rotatable around an axis extending essentially in a lateral-medial direction or essentially in a superior-inferior direction.

The field generator assembly may in some variants be formed as an essentially symmetric component. The field generator assembly may be formed as a mirror-symmetric component relative to a sagittal plane (e.g., of the body of the patient).

As a first variant, the at least one sensor may be stationarily attached relative to (or directly to) a third portion of the at least one first arm. The third portion may be stationarily connected relative to the first portion or be equal to the first portion. The at least one sensor may be an electromagnetic sensor configured to measure the electromagnetic field generated by the field generator. The at least one sensor may be configured to measure a pose of the at least one sensor relative to the field generator. The at least one sensor may be configured to measure a pose of the at least one arm relative to at least one sensor. The third portion may be configured to position the at least one sensor in a first predefined spatial relationship to the first portion when the first portion is in contact with the surface of the body. The first predefined spatial relationship may comprise or consist of a relative pose between the at least one sensor and the first portion. The at least one sensor may be directly attached to or embedded in the at least one arm.

As a second variant, the at least one sensor may be stationarily attached in a second predefined relationship relative to the field generator. The at least one sensor may be an optical or mechanical sensor. The at least one sensor may be configured to measure a pose of the at least one first arm relative to the at least one sensor. The at least one sensor may alternatively or additionally be configured to measure a pose of the field generator relative to the at least one sensor. The at least one sensor may be configured to measure a pose (e.g., an orientation or a rotational position) of the second portion of the at least one arm relative to the field generator. The at least one sensor may be directly attached to or embedded in the casing.

As a third variant, the at least one sensor may be movably attached relative to the field generator and the at least one arm. The at least one sensor may be an optical sensor such as a camera. The at least one sensor may be configured to measure a pose of the at least one first arm relative to the at least one sensor. The at least one sensor may alternatively or additionally be configured to measure a pose of the field generator relative to the at least one sensor.

Note that in the first to third variants, the term "at least one arm" may be replaced one or both of the "second arm" and the "third arm" described above. In other words, one or both of the second arm and the third arm may be configured similarly to or comprised in the at least one first arm.

According to a second aspect, a method of obtaining a relative pose between a surface of a body of a patient and a field generator is provided. The field generator is configured to generate an electromagnetic field and comprised in a field generator assembly, for example the field generator assembly of the first aspect. The method comprises obtaining measurement data. The measurement data describes a measurement of a spatial relationship between at least one first arm of the field generator assembly and the field generator, the at least one first arm being movably attached relative to the field generator. The measurement is acquired by at least one sensor of the field generator assembly while the field generator is attached to the body of the patient and a first portion of the at least one first arm is in contact with the surface of the body of the patient. The method further comprises determining, based on the spatial relationship and at least one predefined geometrical property of the at least one first arm, the relative pose between the surface of the body of the patient and the field generator.

The spatial relationship between the at least one first arm and the field generator may comprise or consist of a relative pose between the at least one first arm and the field generator. The spatial relationship between the at least one first arm and the field generator may comprise or consist of a relative pose between the field generator and a reference part chosen from the at least one sensor stationarily attached relative to the at least one arm, the second portion of the at least one first arm, and an optical marker stationarily attached relative to the at least one first arm. The relative pose between the surface of the body and the field generator may comprise or consist of a pose of at least one point or area on the surface of the body of the patient relative to the field generator. The one or more first portion(s) may be in contact with the at least one point or area on the surface of the body.

The at least one predefined geometrical property may comprise or consist of a relative pose between the at least one sensor and the first portion (e.g., when the first portion is in contact with the surface of the patient's body). The at least one predefined geometrical property may comprise or consist of a relative pose between the first portion and the second portion (e.g., when the first portion is in contact with the surface of the patient's body). The at least one predefined geometrical property may comprise or consist of a relative pose between the first portion and the at least one arm (e.g., when the first portion is in contact with the surface of the patient's body). The at least one predefined geometrical property may comprise a physical property of the at least one arm such as a material, an elasticity, a deformability, a predetermined deformation of the at least one arm when the first portion is in contact with the surface or the like.

The method may further comprise obtaining patient image data describing (e.g., comprising) an image of the body of the patient. The method may further comprise matching the patient image data (e.g., a model surface described by or extracted from the patient image data) to the determined relative pose between the surface of the body of the patient and the field generator. As a result of the matching, a registration between the patient image data and the field generator may be determined or obtained.

Note that in the description of the method of the second aspect, the term "at least one first arm" may be replaced with the "second arm" or the "third arm" described above with reference to the first aspect. In both the description of the first and the second aspect, an attachment of a component X relative to a component Y in one example means an attachment of the component X (e.g., directly) to the component Y.

According to a third aspect, a computer program is provided. The computer program comprises instructions which, when executed on at least one processor, cause the at least one processor to carry out the method according to the second aspect.

According to a fourth aspect, a carrier is provided. The carrier contains the computer program of the third aspect and is one of an electronic signal, an optical signal, a radio signal, or a computer readable storage medium.

BRIEF DESCRIPTION OF THE DRAWINGS

Further details, advantages and aspects of the present disclosure will become apparent from the following embodiments taken in conjunction with the drawings, wherein.

DETAILED DESCRIPTION

In the following description, exemplary embodiments of a surgical navigation system and a surgical navigation method will be explained with reference to the drawings. The same reference numerals will be used to denote the same or similar structural features.

Figure 1:
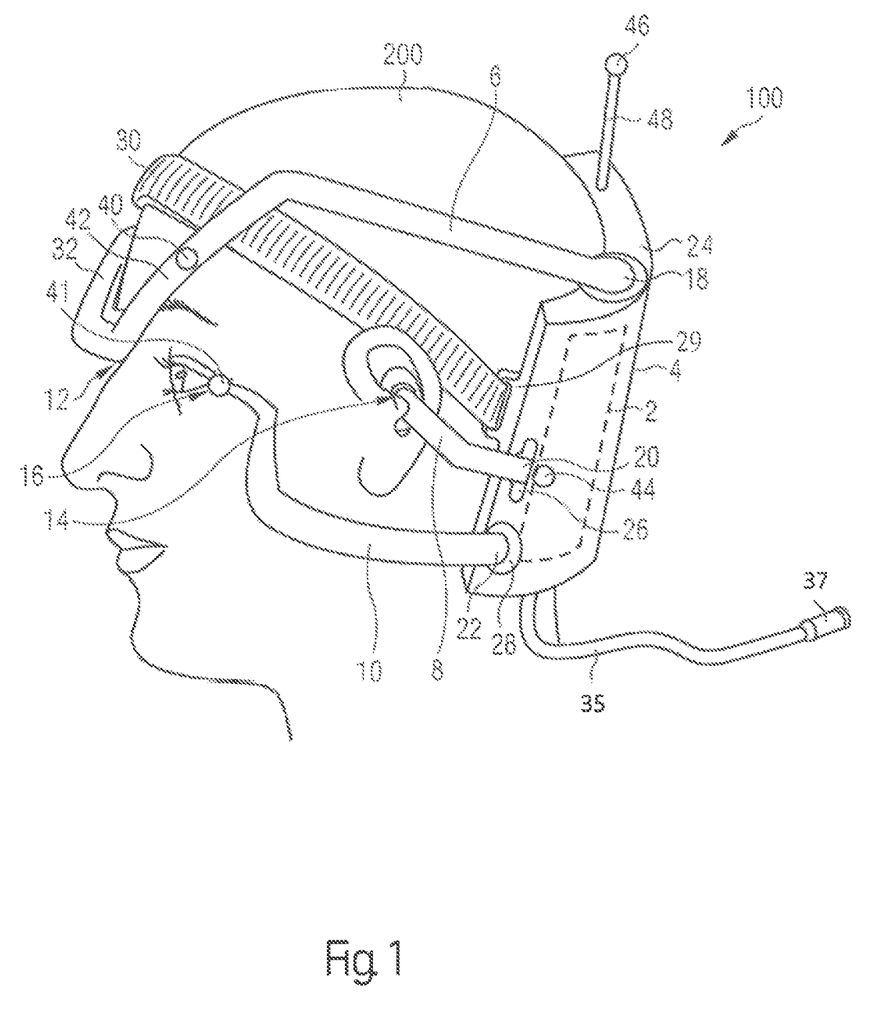
FIG. 1 shows an exemplary embodiment of a field generator assembly attached to a patient's head, according to the present disclosure.

FIG. 1 shows an exemplary embodiment of a field generator assembly 100 attached to a patient's body 200, in particular, a patient's head. The field generator assembly 100 is configured for surgical navigation. The field generator assembly 100 comprises a field generator 2 configured to generate an electromagnetic field (not shown) for electromagnetic navigation. Such an electromagnetic field may be advantageous for cranial surgery (e.g., the placement of a shunt with a stylus that has an electromagnetic sensor). The field generator 2 may be at least one of attached to and encased by a casing 4 of the field generator assembly. Alternatively, the field generator 2 may form the casing 4.

The field generator assembly 100 in the shown example comprises a plurality of first arms 6, 8 and 10. Each of the arms 6, 8 and 10 comprises a first portion 12, 14 and 16 in contact with a surface of the body 200 of the patient. This may mean the first portions 12, 14 and 16 are in (e.g., at least one of constant and stable) contact with the surface, for example for at least an extended period of time, when the field generator 2 is attached via an attachment member to the body 200 of the patient. The first portion 12, 14 and 16 of the respective arm 6, 8 and 10 being in contact with the surface may mean that the first portion 12, 14 and 16 is in a fixed pose relative to the surface for at least an extended period of time.

The first portion 12, 14 and 16 generally may be a first end portion, such as a protrusion or a tip of the respective arm 6, 8 and 10. The first portion 12, 14 and 16 may be tensioned, or biased, against the surface of the body 200 of the patient. The respective arm 6, 8 or 10 may comprise an elastic member tensioning or biasing the first portion 12, 14 and 16 against the surface. For example, the arm 6, 8 or 10 may consist at least partly of a flexible material such as rubber or plastic. For example, the elastic member comprises a spring tensioning or biasing the respective arm against the surface. Alternatively or additionally, the field generator 2 or the casing 4 may comprise the elastic member. This approach may enable a stable placement of the first portion relative to the surface of the patient's body and thus enable an accurate and reliable determination of a relative pose between the surface of the patient's body 200 and the field generator 2.

The first portion 12, 14 and 16 may be in contact with a surface of a predetermined landmark of the body 200 of the patient. The predetermined landmark is preferably characteristic for the patient. The predetermined landmark may be capable of being automatically extracted from patient image data using image analysis. In the shown example, the first portion 12 of the arm 6 is in contact with a surface of a (bridge of a) nose as the predetermined landmark, the first portion 14 of the arm 8 is in contact with a surface of an (inner side of an) earhole as the predetermined landmark, and the first portion 16 of the arm 10 is in contact with a surface of a corner of an eye as the predetermined landmark.

Note that the field generator assembly 100 may be formed as a symmetric component and that at least one first arm may be provided laterally opposite to (e.g., mirror-symmetric with respect to the sagittal plane) the arms 6, 8 and 10 shown in FIG. 1. In this case, the at least one laterally opposite first arm may comprise a first portion in contact with the surface of an (inner side of an) an earhole laterally opposite to the earhole shown in FIG. 1 as the predetermined landmark (the earhole of the right ear), or with a surface of a corner of an eye laterally opposite to the eye shown in FIG. 1 as the predetermined landmark (the right eye). Such a landmark may enable determining a relative pose between the surface of the body 200 and the field generator 2 with a high accuracy, even in case of different patients.

The arms 6, 8 and 10 each further comprise a second portion 18, 20 and 22 movably attached relative to the field generator 2. The second portion 18, 20 and 22 may be a second end portion, an attachment or a coupling element of the respective arm 6, 8 and 10. In the shown example, the second portion 18 of the arm 6 is attached to an essentially tube-shaped component 24 having a longitudinal axis extending essentially in the lateral-medial direction. The component 24 may be stably (e.g., immovably or stationarily) attached relative to the field generator 2 and arranged on a superior side relative to the field generator 2. The component 24 may be stably attached to the casing 4 or may be part of the casing 4. The arm 6 may be configured to be rotatable only around an axis extending essentially in a lateral-medial direction. Also, in the shown example, the second portion 20 of the arm 8 is movably connected relative to the field generator in a slot 26 of the casing 4. The arm 8 may be configured to be rotatable only around an axis extending essentially in a superior-inferior direction. Still further, in the shown example, the second portion 22 of the arm 10 is movably connected relative to the field generator in a hole 28 of the casing 4. The arm 8 may be configured to be rotatable around both an axis extending essentially in a superior-inferior direction and an axis extending essentially in a lateral-medial direction. In another variant, each of the arms 6, 8 and 10 is rotatable in all directions relative to the field generator 2. This configuration may enable a compact construction of the field generator assembly 100, an easy placement of the field generator assembly 100 on the patient's body 200, and a stable contact between the first portion(s) 12, 14, 16 and the surface of the body 200.

The field generator 2 in the shown example is attached (e.g., relative) to a posterior side of the head of a patient's body 200 by the attachment member. The attachment member comprises a headband 30. The headband 30 is preferably adjustable in size or flexible to fit on heads of different patients. The headband 30 is attached to a band connection part 29 of the casing 4. In one variant, the attachment member comprises or consists of one or more of the arms comprised in the field generator assembly 100 (e.g., the arms 6, 8 and 10). That is, one or more, for example all of the arms comprised in the field generator assembly 100 may attach the field generator 2 to the body 200 of the patient. One may say that the body 200 is positioned, clamped or jammed between the casing 4 and the arms comprised in the field generator assembly 100, when the field generator 2 is attached to the body 200. This may enable a secure attachment of the field generator 2 relative to the patient's body 200 and optionally avoid the need for additional attachment means such as the headband 30.

The field generator assembly 100 further comprises at least one sensor 40, 41, 44, 46 configured to measure a spatial relationship between the at least one first arm (e.g., one or more of the arms 6, 8 and 10) and the field generator 2. The spatial relationship may comprise or consist of a pose (i.e., at least one of a position and an orientation) of (e.g., a part of) the at least one first arm relative to the field generator 2.

Thus, the at least one sensor 40, 41, 44, 46 provides a measurement based on which a relative pose of points or regions of the surface (e.g., of the predefined landmarks) of the patient's body 200 may be determined relative to the field generator 2. The field generator assembly 100 therefore may enable a fast determination of a pose of surface of a patient's body 200 relative to the field generator 2 with a high accuracy.

As a first variant of the at least one sensor, the sensor 40 is stationarily (i.e., unmovably or stably) attached relative to a third portion 42 of the arm 6 and configured to measure a pose of the sensor 40 relative to the field generator 2. The sensor 40 is for example an electromagnetic sensor configured to detect an electromagnetic field generated by the field generator 2 to measure its pose relative to the field generator 2. The sensor 40 in this case comprises one or more coils configured to measure the electromagnetic field. Each coil may be electrically connectable via dedicated wiring (not shown) to a localizer of an electromagnetic tracking or navigation system (also not shown).

The sensor 40 may be embedded in the arm 6. In this variant, the third portion 42 may be configured to position the sensor 40 in a first predefined spatial relationship to the first portion 12 when the first portion 12 is in contact with the surface of the body 200. In other words, the arm 6 may be configured such that the sensor 40 is in the first predefined spatial relationship to the first portion 12 when the first portion 12 is in contact with the surface of the body 200. The first predefined spatial relationship may comprise or consist of a first predefined pose of the sensor 40 relative to the first portion 12.

In an example of the first variant, the third portion 42 may be stationarily connected relative to the first portion 12. The stationary connection may then define the first predefined spatial relationship.

In another example of the first variant, the third portion 42 may be movably connected relative to the first portion 12. For instance, the arm 6 may comprise an elastic or flexible material, or may comprise one or more joints. The arm 6 may be configured such that it is (e.g., reversibly) deformed in a predetermined manner and by a predetermined amount, for example by moving one or more of the joints or by bending the elastic or flexible material, when the first portion 12 is in contact with the surface.

That is, a predetermined deformation of the arm 6, describing a deformation of the arm 6 when the first portion 12 is in contact with the surface, may define (e.g., together with a predefined geometrical property of the arm 6) the first predetermined spatial relationship of the sensor 40 relative to the first portion 12.

As a second variant of the at least one sensor, the sensor 41 is stationarily attached relative to the first portion 16 of the arm 10 and configured to measure a pose of the sensor 41 relative to the field generator 2. The sensor 41 is for example an electromagnetic sensor configured to detect an electromagnetic field generated by the field generator 2 to measure its pose relative to the field generator 2. The sensor 41 may be attached directly to the first portion 16 of the arm 10. In these cases, the pose of the sensor 41 relative to the field generator 2 may correspond to a pose of the first portion 16 relative to the field generator 2. As in in the case of the sensor 40, the sensor 41 may be an electromagnetic sensor, for example embedded in the arm 10.

One or more of the at least one arm 6, 8, 10 may comprise more than one sensor 40, 41, each of which is stably attached relative to a certain portion of the at least one arm 6, 8, 10, the certain portion being optionally configured to be in contact with the surface of the body 200 of the patient when the field generator 2 is attached to the patient's body 200. The certain portions may be movably connected relative to one another. That is, the pose of the at least one arm 6, 8, 10 may be described by more than one sensor measurement and/or the at least one arm 6, 8, 10 may define more than one point or area on the surface of the patient's body 200 which may then be used to determine a pose of the surface relative to the field generator 2.

In one example, the headband 30 comprises an electromagnetic sensor (not shown) configured to detect an electromagnetic field generated by the field generator 2. The headband 30 may then comprise a first portion, e.g., a protrusion, a contact pad, or a segment of the headband 30, which is configured to be in contact with the surface of the body 200 of the patient when the field generator 2 is attached to the body 200. The sensor comprised in the headband 30 may be configured similarly to the sensor 40 (e.g., arranged at the first portion) or the sensor 41 (e.g., arranged in a fixed spatial relationship relative to the first portion) described herein for enabling determining a relative pose between the first portion comprised in the headband 30 and the field generator 2.

As a third variant of the at least one sensor, the sensor 44 is stationarily attached in a second predefined relationship relative to the field generator 2. The second predefined spatial relationship may comprise or consist of a second predefined pose of the sensor 44 relative to the field generator 2. For example, the sensor 44 is stationarily attached to the casing 4. The sensor 44 may be embedded in the casing 4. The sensor 44 may be configured to measure a pose of the (e.g., second portion 20 of the) arm 8 relative to the field generator 2. The sensor 44 may be an optical or mechanical sensor configured to measure a (e.g., rotational) position of the second portion 20 relative to the field generator 2. The sensor 44 may be configured to measure the pose of the arm 8 relative to the casing 4, wherein the casing 4 is in a known spatial relationship to the field generator 2.

As a fourth variant of the at least one sensor, the sensor 46 is movably attached relative to the field generator 2 and the at least one arm 6, 8, 10. The sensor 46 may be attached via a coupling element 48 to the casing 4. The sensor 46 may be an optical sensor such as a camera. The sensor 46 may be configured to measure a pose of one or more of the arms 6, 8 and 10 relative to the sensor 46. The sensor 46 may be further configured to measure a pose of the field generator 2 relative to the sensor 46. Alternatively or additionally, the sensor 46 may be configured to measure a pose of the casing 4 relative to the sensor 46, and determine the pose of the field generator 2 relative to the sensor 46 based on a known relative pose between the casing 4 and the field generator 2. One or more of the arms 6, 8 and 10, the casing 4 or the field generator 2 may be stationarily attached to a respective passive or active optical tracker detectable by the sensor 46. Alternatively or additionally, the sensor 46 may extract the pose of an arm from an acquired image based on image analysis and/or feature recognition.

The field generator assembly 100 further comprises a cable 35 and a plug 37 connected to the cable 35. The cable 35 connects the field generator 2 with an external power supply. Additionally or alternatively, the cable 35 transmits a measurement signal of the at least one sensor 40, 41, 44, 46 to a processor of a tracking system or an apparatus as described herein.

Figure 2:
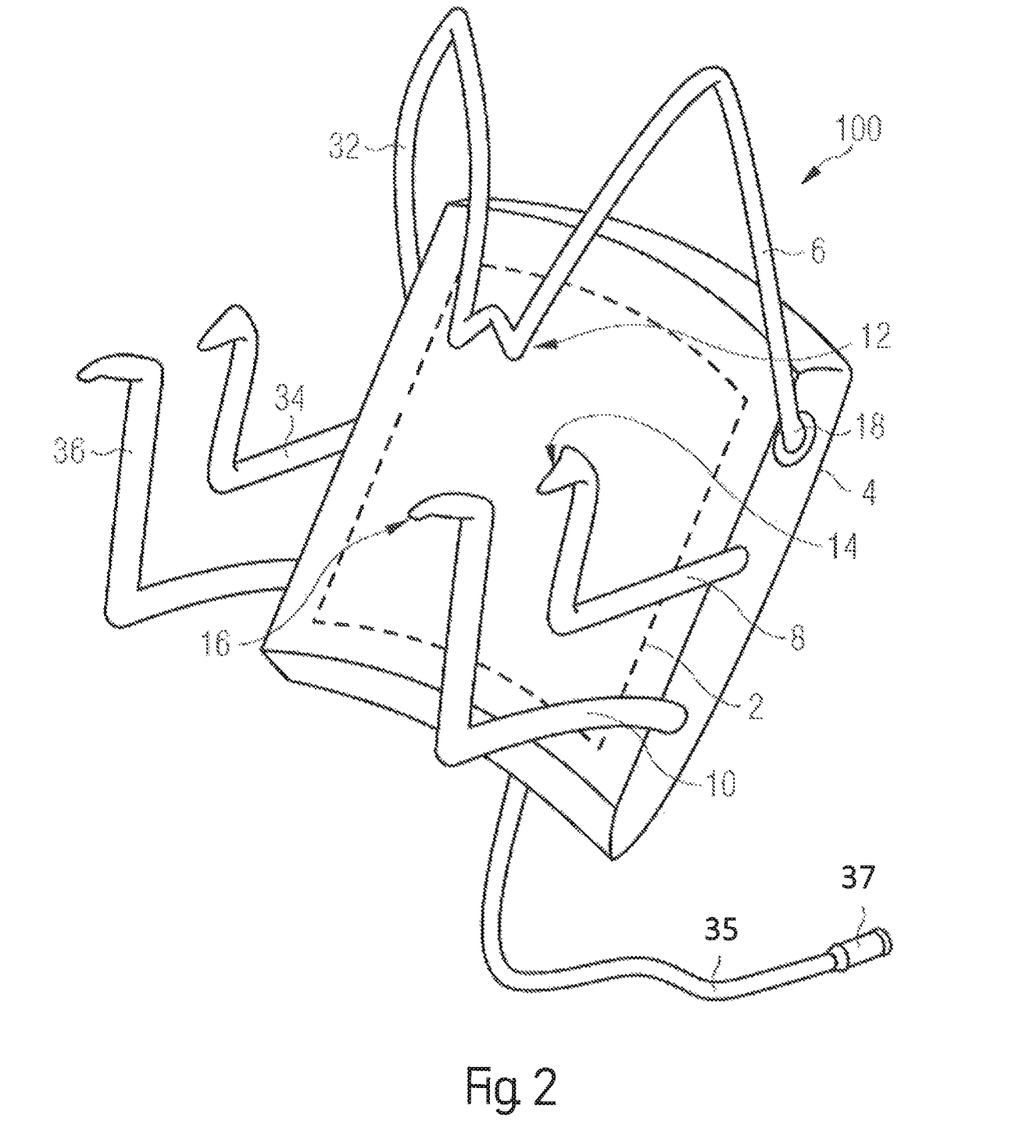
FIG. 2 shows the exemplary embodiment of the field generator assembly according to the present disclosure.

FIG. 2 shows the exemplary embodiment of the field generator assembly 100 according to the present disclosure, without being attached to a patient's body. In this example of the field generator assembly 100, the first arm 6 is directly attached to the casing 4. In this example, the casing 4 comprises a front side to be oriented towards the patient's body 200, a back side opposite to the front side, and two opposite lateral sides, wherein all arms comprised in the field generator assembly 100 are coupled to the casing 4 on its lateral sides. Other attachment positions of the arms are also possible.

The field generator assembly 100 comprises a second arm 32 connected to the first arm 6 to be movable together with the first arm 6. As indicated in FIG. 2, the second arm 32 may be movably attached relative to the field generator 2. The first arm 6 and the second arm 32 may each comprise a first portion configured to be in contact with the surface of the patient when the field generator 2 is attached to the patient, and the respective first portions may be directly connected with one another via a coupling portion attaching the second arm 32 to the first arm 6. The first arm 6 may be connected with the second arm 32 via the first portion 12. The connected first and second arm 6, 32 may form a substantially bow-shaped part. The second arm 32 may increase rigidity and ensure a stable placement of the first portion 12 of the first arm 6 on the surface of the body 200.

FIG. 2 shows two third arms 34 and 36. The third arms 34 and 36 and the second arm 32 are located on a first (e.g., lateral) side relative to the field generator 2, whilst the first arms 6, 8 and 10 are located on a second (e.g., lateral) side relative to the field generator 2. The first side is opposite to the second side relative to the field generator 2. It can be seen from FIGS. 1 and 2 that the field generator assembly 100 may be formed as an essentially symmetric component. In particular, the field generator assembly 100 may be formed as a mirror-symmetric component relative to a sagittal plane. Such a configuration may be advantageous as the human body is also essentially mirror-symmetric. In particular, as noted above, landmarks of a same type (e.g., ear holes or corners of eyes) may be mirror-symmetric to the sagittal plane. Also, such a configuration may increase symmetry of the electromagnetic field generated by the field generator 2.

One or more of the arms 6, 8, 10, 32, 34, 36 may be removably attached to the casing 4. One or more of the arms 6, 8 and 10 may be formed as a sterilizable component or as a single-use disposable component. Note that one or more of the second and third arms 32, 34, 36 may be configured similarly as the first arms 6, 8, 10, in particular, may comprise the first portion configured to contact the surface of the patient's body 200 and the second portion movably attaching the respective second or third arm relative to the field generator 2. One or more of the second and third arms 32, 34, 36 may correspond to the at least one first arm described herein.

Figure 3:
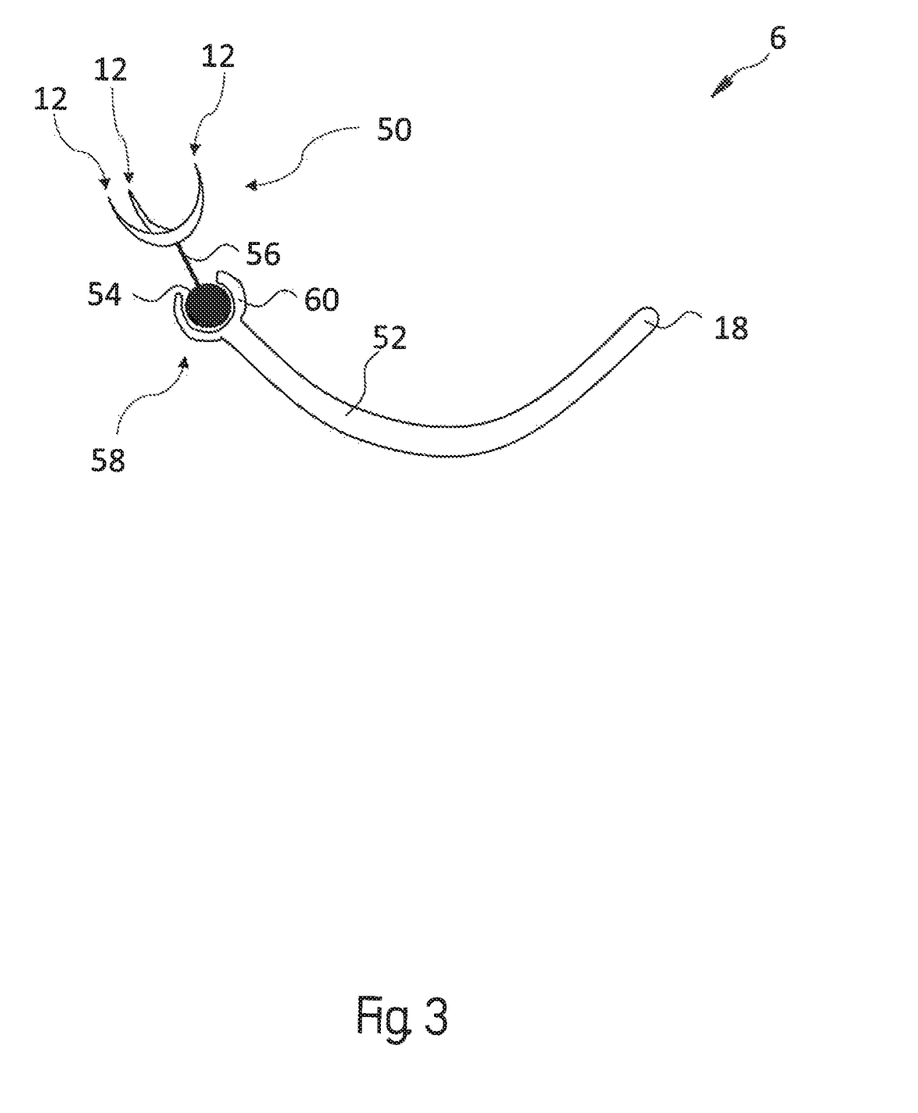
FIG. 3 shows an exemplary embodiment of an arm comprised in the exemplary embodiment of the field generator assembly according to the present disclosure.

FIG. 3 shows an exemplary embodiment of the arm 6 of the field generator assembly 100. In this case, the arm 6 is not connected to another arm. The shown arm 6 comprises the first portion 12 multiple times, in particular exactly three times. The arm 6 comprises a hand 50 having three fingers, each finger having a fingertip configured to be in contact with the surface of the body 200 when the field generator 2 is attached to the body 200. That is, each of the three fingers of the hand 50 comprises (e.g., an instance of) the first portion 12.

The hand 50 may be movably connected to an element 52 of the arm 6 comprising the second portion 18. In the shown example, the hand 50 is connected to a ball 54 via a connecting member 56. The ball 54 forms part of a ball joint 58 movably coupling the hand 50 to the element 52 of the arm 6. The ball 54 is rotatably held in place by a socket 60 of the ball joint 58. The socket 60 is formed on an end of the element 52 opposite to the end at which the second portion 22 is located. Other ways of movably connecting the hand 50 to the element 52 are also possible. The sensor 40 comprised in the arm 6 (not shown in FIG. 3) may be rigidly attached relative to the hand 50. For example, the sensor 40 is embedded in or rigidly attached to the connecting member 56. In this case, the third portion 42 described herein may be formed by at least a part of the connecting member 56 and by the fingers of the hand 50. Based on the first predefined spatial relationship(s) between the sensor 40 and each of (e.g. the instances of) the first portion(s) 12 of the hand 50, poses of each of (e.g., the instances of) the first portion(s) 12 relative to the field generator 2 can be determined based on a measurement by the sensor 40, wherein the measurement by the sensor is indicative of a relative pose between the sensor 40 and the field generator 2.

The first portions 12 may not only be comprised in the fingers of the hand 50, but also in additional protrusions or contact tips formed on the element 52 of the arm 6. In this case, multiple sensors 40, 41, 44, 46 may be provided to determine relative poses between the plurality of first portions 12 of the arm 6 relative to the field generator. For instance, a first sensor 40 may be embedded in the element 52 of the arm 6 to enable determining a pose of a first portion 12 which is comprised in a protrusion formed on the element 52 relative to the field generator, while an additional second sensor 40 may be embedded in the connecting member 56 for enabling determining relative poses between the first portions 12, comprised in the fingers of the hand 50, and the field generator 2. In other words, the arm 6 may comprise a plurality of first portions 12 and one or more sensors may be provided for determining relative poses between all of the first portions 12 and the field generator 2 based on the sensor measurements and, for example, the first predefined spatial relationship.

The hand 50 may alternatively be fixed relative to the element 52 of the arm 6, for example by rigidly attaching the connecting member 56 to the element 52. The sensor 40 may be arranged and configured as explained above with reference to the sensors 41, 44 or 46. Such sensor arrangements and configurations also enable determining poses between each of the first portions 12 of the arm 6 relative to the field generator 2.

In FIG. 3, the arm 6 is shown as an example, although it is noted that one or more of the arms 6, 8, 10, 32, 34 and 36 comprised in the field generator assembly 100 may have a similar structure. In other words, one or more of the arms 6, 8, 10, 32, 34 and 36 may comprise a plurality of first portions configured to be in contact with the surface of the body 200 when the field generator 2 is attached to the body 200. In case it is referred to the "first portion" of an arm (e.g., the first portion 12, 14 or 16) herein, it is to be understood that each, all or at least one of the plurality of first portions comprised in the arm may be meant.

Figure 4:
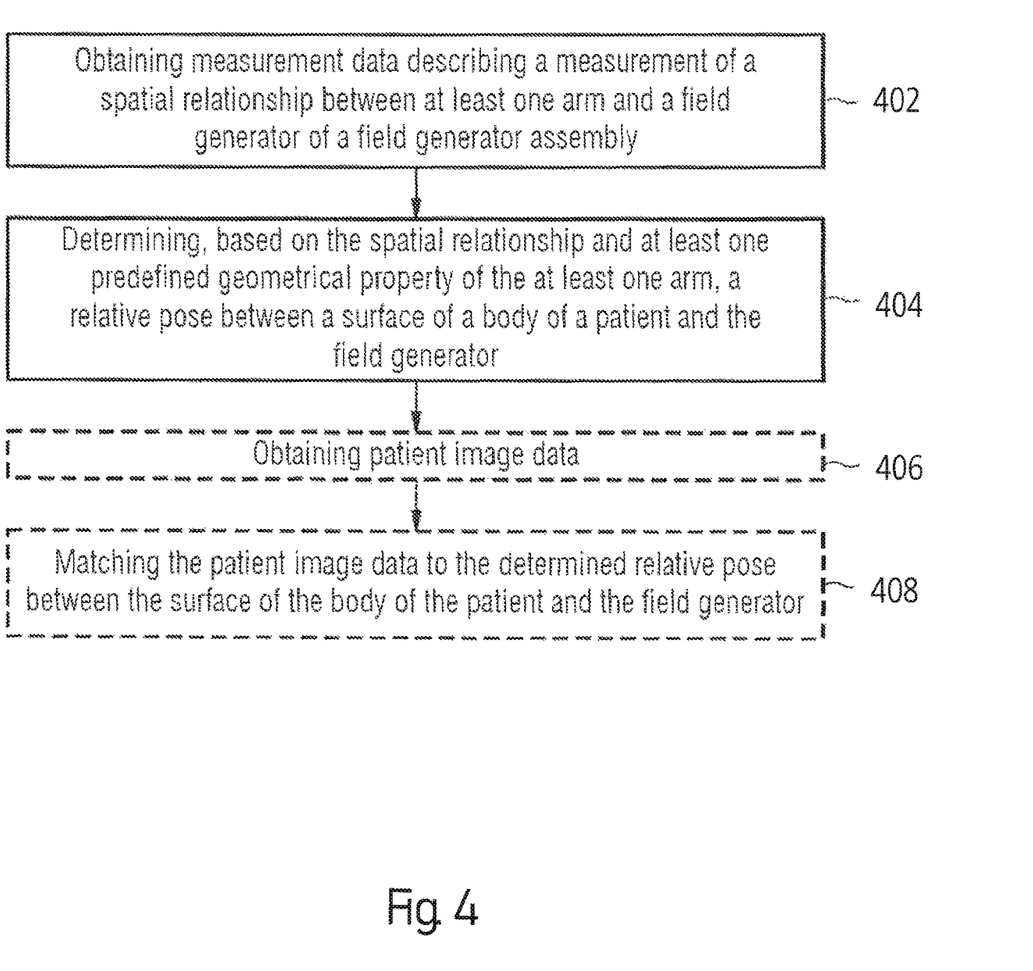
FIG. 4 shows an exemplary embodiment of a method according to the present disclosure.

FIG. 4 shows an exemplary embodiment of a method of obtaining a relative pose between a surface of a body of a patient and a field generator configured to generate an electromagnetic field and comprised in a field generator assembly. The method embodiment will be explained with reference to the embodiment of the field generator assembly 100 described above with reference to FIGS. 1 to 3.

The method comprises a step 402 of obtaining measurement data describing a measurement of a spatial relationship between the at least one first arm 6, 8, 10 of the field generator assembly and the field generator 2, the at least one first arm 6, 8, 10 being movably attached relative to the field generator 2. The measurement is (or was) acquired by at least one sensor 40, 41, 44, 46 of the field generator assembly 100 while the field generator 2 is (or was) attached to the body 200 of the patient and (e.g., each of) the first portion(s) 12, 14, 16 of the at least one first arm 6, 8, 10 is (or was) in contact with the surface of the body 200 of the patient. The measurement data may further describe a measurement of a spatial relationship between the sensor comprised in the headband 30 and the field generator 2. The method also comprises a step 404 of determining, based on the spatial relationship and at least one predefined geometrical property of the at least one first arm 6, 8, 10, the relative pose between the surface of the body 200 of the patient and the field generator 2.

The step 404 may further comprise determining, based on a predefined relative pose of the sensor comprised in the headband 30 and the first portion comprised in the headband 30, a relative pose between the first portion comprised in the headband 30 and the field generator 2. The relative pose determined in step 404 may be determined by determining a pose of one or more points or areas on the surface of the body 200 relative to the field generator 2, which correspond to poses of respective first portions of one or more of the arms 6, 8, 10, 32, 34, 36 and, optionally, of the headband 30, relative to the field generator 2. In other words, the poses of the first portions 12, 14, 16 relative to the field generator 2 can be assumed to be equal to the poses of the one or more points or areas on the surface of the body 200 relative to the field generator, with which points or areas the first portions 12, 14, 16 are in contact. The relative pose between the first portions 12, 14, 16 and the field generator 2 may thus be determined as the relative pose between the surface of the body 200 and the field generator 2. For example, only one point may be determined in step 404 as the relative pose, wherein the point lies on a surface of a nose bridge of the patient and corresponds to a position of the first portion 12 of the arm 6 relative to the field generator 2. In other words, the relative pose determined in step 404 may define a position of a point on the surface of the nose bridge of the patient relative to the field generator 2. The relative pose determined in step 404 may be determined based on a plurality of (e.g., exactly three or more than three) points or areas on the surface of the body 200 of the patient corresponding to first portions of one or more of the arms 6, 8, 10, 32, 34, 36.

The measured spatial relationship preferably comprises or consists of a pose of the at least one arm 6, 8, 10 relative to the field generator 2.

In a first variant, the measured spatial relationship may comprise or consist of a pose of the sensor 40 relative to the field generator 2. In this case, the geometrical property may comprise or consist of the first predefined spatial relationship described above. For example, the sensor 40 may embedded in the connecting member 56 of the hand 50 as described above and the first predefined spatial relationship comprises relative poses between the sensor 40 and each of the first portions 12 of the hand 50. The geometrical relationship may comprise the predetermined deformation described above.

In a second variant, the measured spatial relationship may comprise or consist of a pose of the sensor 41 relative to the field generator 2. In this case, the geometrical property may indicate that the sensor 41 is arranged at the first portion 16 of the arm 10 and thus, that a pose of the sensor corresponds to a pose of the first portion 16.

In a third variant, the measured spatial relationship may comprise or consist of a pose of the second portion 20 of the arm 8 relative to the field generator 2, as measured by the sensor 44. The geometrical relationship may comprise at least one of a spatial relationship between the second portion 20 and the first portion 14 and the predetermined deformation described above.

In a fourth variant, the measured spatial relationship may comprise or consist of a pose of the at least one arm 6, 8, 10 relative to the sensor 46 described above, and a pose of the field generator 2 relative to the sensor 46. As noted above, the pose of the field generator 2 relative to the sensor 46 may be determined based on a measured pose of the casing 4 relative to the sensor 46 and a known pose of the field generator 2 relative to the casing 4. Alternatively or additionally, the pose of the field generator 2 relative to the sensor 46 may be directly measured by the sensor 46, for example using image analysis conducted on an image acquired by the sensor 46 in case the sensor 46 is a camera. The geometrical relationship may comprise a spatial relationship of the first portion 12, 14, 16 of the at least one arm 6, 8, 10 relative to the at least one arm 6, 8, 10 and, optionally, the predetermined deformation described above.

The method may further comprise a step 406 of acquiring patient image data comprising or describing an image of the body 200 of the patient. The patient image data may be CT or MR image data of the patient. The method may further comprise a step 408 of matching the determined relative pose between the surface of the body 200 of the patient and the field generator 2 (or the determined poses of the points or areas of or on the surface of the body 200 relative to the field generator 2) with the patient image data to obtain a registration between the patient image data and the patient's body 200. In particular, a model body surface extracted from the patient image data may be matched with the determined poses of points or areas of the surface of the body 200 which have been contacted by or which correspond to poses of the first portions 12, 14, 16 of at least one of the arms 6, 8, 10, 32, 34, 36 when acquiring the sensor measurements. As a result of the step 408, a registration between the patient image data and the field generator 2 may be obtained.

The method may enable a reliable and accurate determination of the relative pose between the surface of the body 200 of the patient and the field generator 2, and, optionally, a reliable and accurate determination of the registration between the patient image data and the field generator 2.

Figure 5:
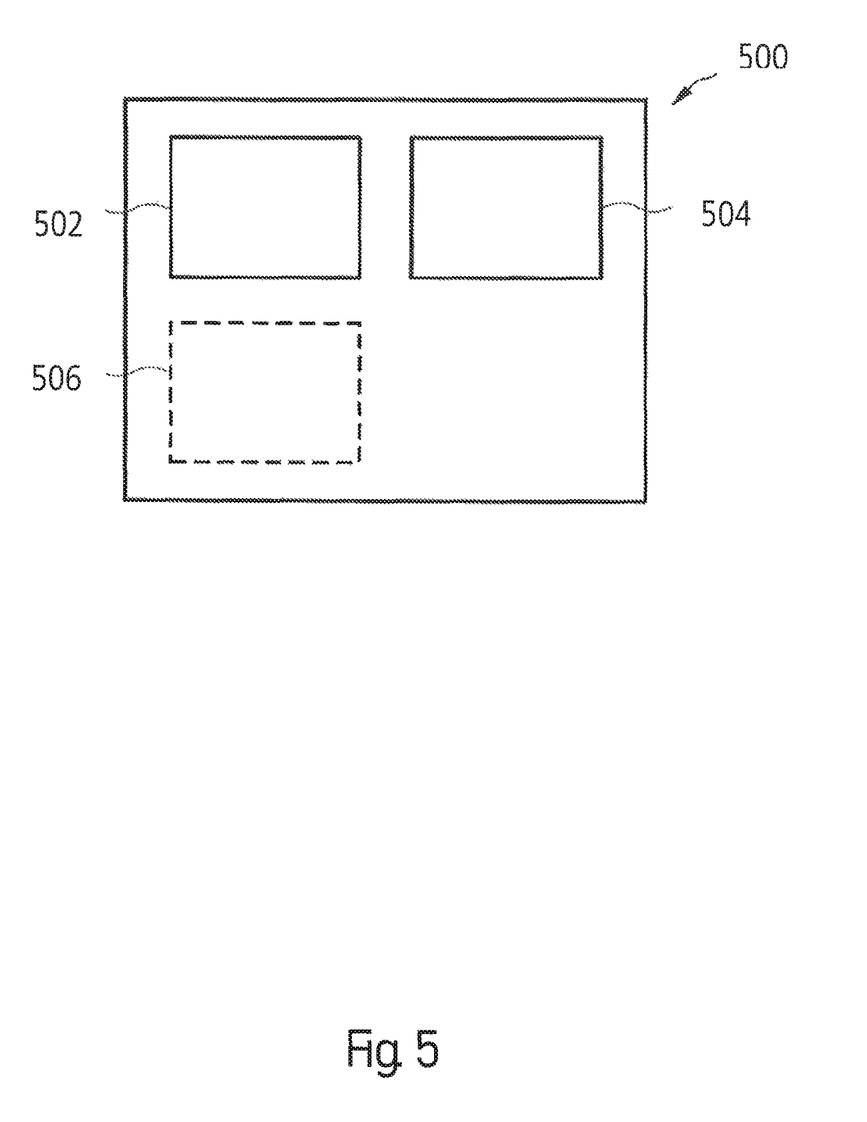
FIG. 5 shows an exemplary embodiment of an apparatus according to the present disclosure.

FIG. 5 shows an exemplary embodiment of an apparatus 500 according to the present disclosure. The apparatus comprises a processor 502, a memory 504 and may further comprise an interface 506. The memory 504 is a computer readable storage medium and contains a computer program comprising instructions which, when executed on the processor 502, cause the processor 502 to carry out the method described herein. The interface may be configured to obtain, receive, retrievably provide or send information such as the measurement data and/or the relative pose between the surface of the body of the patient and the field generator.

The invention is defined by the appended claims. Variations and combinations of the examples and exemplary embodiments described herein are possible, as will be apparent to the person skilled in the art.

The invention claimed is:

1. A field generator assembly for surgical navigation, the field generator assembly comprising:
 a field generator configured to generate an electromagnetic field;
 an attachment member configured to attach the field generator to a body of a patient;
 at least one first arm comprising:
  a first portion configured to be in contact with a surface of the body of the patient when the field generator is attached to the body, and
  a second portion movably attached relative to the field generator; and
 at least one sensor configured to measure a spatial relationship between the at least one first arm and the field generator, wherein at least one of the following conditions (a) to (d) is fulfilled:
 (a) the field generator assembly further comprises a third arm, wherein the at least one first arm and the third arm are located on opposite sides relative to the field generator;
 (b) the attachment member is configured to attach the field generator to a posterior side of a head of the patient;
 (c) the at least one first arm is configured to be rotatable around an axis extending essentially in a lateral-medial direction or essentially in a superior-inferior direction; and (d) the field generator assembly is formed as an essentially mirror-symmetric component relative to a sagittal plane.

2. The field generator assembly of claim 1, wherein the first portion is a first end portion of the at least one first arm.

3. The field generator assembly of claim 1, wherein the attachment member comprises or consists of the at least one first arm.

4. The field generator assembly of claim 1, wherein the first portion is configured to be tensioned against the surface of the body of the patient when the field generator is attached to the body.

5. The field generator assembly of claim 1, wherein the first portion is configured to be in contact with a surface of a predetermined landmark of the body of the patient when the field generator is attached to the body.

6. The field generator assembly of claim 1, wherein the at least one first arm comprises multiple first portions.

7. The field generator assembly of claim 1, further comprising a second arm connected to the first arm so as to be movable together with the first arm.

8. The field generator assembly of claim 1, wherein the at least one sensor is configured to measure a pose of the at least one first arm relative to the at least one sensor and to measure a pose of the field generator relative to the at least one sensor.

9. A field generator assembly for surgical navigation, comprising:
- a field generator configured to generate an electromagnetic field;
- an attachment member configured to attach the field generator to a body of a patient;
- at least one first arm comprising:
  - a first portion configured to be in contact with a surface of the body of the patient when the field generator is attached to the body, and
  - a second portion movably attached relative to the field generator; and
- at least one sensor configured to measure a spatial relationship between the at least one first arm and the field generator,
- wherein the at least one sensor is stationarily attached relative to a third portion of the at least one first arm and configured to measure a pose of the at least one sensor relative to the field generator.

10. The field generator assembly of claim 9, wherein the third portion is configured to position the at least one sensor in a first predefined spatial relationship to the first portion when the first portion is in contact with the surface of the body.

11. The field generator assembly of claim 9, wherein the third portion is stationarily connected relative to the first portion.

12. A field generator assembly for surgical navigation, comprising:
- a field generator configured to generate an electromagnetic field;
- an attachment member configured to attach the field generator to a body of a patient;
- at least one first arm comprising:
  - a first portion configured to be in contact with a surface of the body of the patient when the field generator is attached to the body, and
  - a second portion movably attached relative to the field generator; and
- at least one sensor configured to measure a spatial relationship between the at least one first arm and the field generator,
- wherein the at least one sensor is stationarily attached in a second predefined relationship relative to the field generator.

13. The field generator assembly of claim 12, wherein the at least one sensor is configured to measure a pose of the second portion of the at least one first arm relative to the field generator.

* * * * *